United States Patent [19]

Tayot et al.

[11] Patent Number: 4,543,209
[45] Date of Patent: Sep. 24, 1985

[54] PROCESS FOR PREPARING GLOBIN FROM HAEMOGLOBIN AND GLOBIN OBTAINED BY THIS PROCESS

[75] Inventors: Jean L. Tayot, La Tour de Salvagny; Jean L. B. Veron, St. Egrève, both of France

[73] Assignee: Institut Merieux

[21] Appl. No.: 628,285

[22] Filed: Jul. 6, 1984

[30] Foreign Application Priority Data

Jul. 7, 1983 [FR] France ................. 83 11324

[51] Int. Cl.$^4$ ............ A61K 35/14; A61K 37/04; C07C 103/52; C07G 7/00
[52] U.S. Cl. ............ 260/112 B; 260/112.5 R; 260/115; 424/101
[58] Field of Search ............ 260/112.5 R, 112 B, 260/115; 424/101

[56] References Cited

U.S. PATENT DOCUMENTS

| | | | |
|---|---|---|---|
| 2,460,550 | 2/1949 | Strumia et al. | 260/112 B |
| 4,098,780 | 7/1978 | Lindroos | 260/112.5 R |
| 4,330,463 | 5/1982 | Luijerink | 260/112 B |
| 4,376,727 | 3/1983 | Sato et al. | 260/112 B |
| 4,431,581 | 2/1984 | Lindroos | 260/112 B |
| 4,439,357 | 3/1984 | Bonhard et al. | 260/112 B |
| 4,446,066 | 5/1984 | Luijerink | 260/112.5 R X |
| 4,473,494 | 9/1984 | Tye | 260/112 B |

FOREIGN PATENT DOCUMENTS 2505844 11/1982 France.

OTHER PUBLICATIONS

Teale, Biochim. Bioplysica Acta, 35, 543 (1959).
Rossi-Fanelli et al., Biochim. Biophysica Acta, 30, 608-615 (1958).
Strumia et al., J. of Lab. and Clin. Medicine, 37(6), 959-968 (1951).
Liautaud et al., Coll—Developments in Biological Standardization, vol. 27, 1974, 107-114.
Anson et al., J. Gen. Physiol., 13(1930), 469-476.
J. of Lab. and Clin. Medicine (1952), 40(2), 211-222, Strumia et al.

*Primary Examiner*—Howard E. Schain
*Attorney, Agent, or Firm*—Larson and Taylor

[57] ABSTRACT

An 80% alcoholic solution of haemoglobin having a pH close to 3 is adsorbed on active charcoal at less than 20° C. while continuously stirring and the globin solution obtained is separated out by centrifuging or filtering. The globin obtained is depigmented.

19 Claims, No Drawings

PROCESS FOR PREPARING GLOBIN FROM HAEMOGLOBIN AND GLOBIN OBTAINED BY THIS PROCESS

The present invention relates to a new process for preparing globin from haemoglobin and to the globin obtained by this process.

The works of Anson and Mirsky (*J. Gen. Physiol.* 13,469–476) published in 1930 have shown that it is possible to separate the pigment of the haemoglobin (haem) by the method employing acid acetone. Thus various human or animal haemoglobins have already been converted into globin. Two variations of this process are usually employed on the laboratory scale, both of which are based on the low affinity of the haem for the globin having an acid pH.

One of the processes is the acid acetone method (see for example *ROSSI*-FANELLI et coll. (1958) *Biophys. Bioch. Acta* 30, 608–615). This process comprises adding a volume of haemoglobin at 30 g/l to 20 to 30 volumes of acetone at −20° C. containing 3 ml of 2N HCl per liter, stirring at −20° C. and then centrifuging, the precipitate of globin being redissolved in water and dialyzed against distilled water.

This globin solution is only stable when its pH remains acid so that there was proposed (*STRUMIA et coll. J. of Lab. and Clin. Medicine*, 37,6 959–968 in 1951) a mild hydrolysis of the globin at an alkaline pH so as to render the molecule soluble at a neutral pH.

The second process is the butanone-acid process according to *TEALE* 1959 *Bioch. Biophys. Acta* 35,543. Substituting butanone which is only slightly soluble in water for the acetone permits a rapid separation into two phases of the haem (ketonic phase) and the globin (aqueous phase).

However, these two processes do not lend themselves to an industrial application owing to the considerable volumes of organic solvents which would have to be employed and the consequential risks of accidents. Further, the final globin obtained contains appreciable amounts of chemical residues which are dangerous in its utilization for food purposes, in the case of the animal globin, or therapeutic utilization, in the case of human globin.

Consequently, a number of other processes have already been proposed for the purpose of obtaining globins of animal origin for food application.

The Japanese patent application No. 55.008261 filed on Jan. 29, 1980 by Y. SATO and S. HAYAKAWA proposes a selective adsorption of the pigment of the haemoglobin with an acid pH with CM cellulose. This process avoids the use of alcohol and solvents but has the drawback of not decolouring sufficiently the haemoglobin for therapeutic applications, owing to the toxicity of the haem.

The Russian patent No. 25 44365/28-13 of Aug. 8, 1977 filed by K. A. LOBUNETS discloses a globin preparation for therapeutic use from a haemolysate of human red globules. It concerns a treatment employing peroxide of hydrogen in the hot state, which has the drawback of seriously denaturing the protein.

In 3 patent applications filed in Sweden, namely:
No. 67 407882-5 of June 14, 1974,
No. 75 13987-3 of Dec. 11, 1975 and
No. 80 02591-9 of Apr. 3, 1980

P. G. LINDROOS proposes various treatments in alcoholic solution at an acid pH in the cold state (see French Pat. No. 2 351 604). Depending on the nature and the concentration of the added salts, the globin precipitates or remains in solution in a selective manner and is separated from the pigments which become agglomerated. The addition of imidazole or related molecules facilitates this separation.

In all cases, the globin obtained is too rich in pigments to be of use in therapeutics.

The closely related processes proposed by P. ESPENAN in the French Pat. No. 81 09890 of May 14, 1981 or by J. H. LUIJERINK in the British Pat. No. 1,977,278 of Dec. 22, 1978 have the same drawbacks.

Now, it would be of great interest to have available large quantities of perfectly depigmented and non-denatured globin, in particular for therapeutic use as a substitute for plasma, as already mentioned in: *SAMPLE et coll. The J. of Lab. and Clin. Medicine* (1952), 40,2 206–210 *STRUMIA et coll. The J. of Lab and Clin. Medicine* (1952), 40,2 211–222.

The present invention therefore proposes to overcome these drawbacks and to provide a new process for preparing globin from haemoglobin which permits, under industrial conditions, cheaply obtaining a globin which is extremely purified and but little or not denatured.

A particular object of the invention is to provide a process which permits the industrial manufacture of globins of use in therapeutics.

Another object of the invention is to provide a process which can be used for obtaining globin from haemoglobin coming from very different sources which may be in particular:
human placental haemolyzed blood;
some other human haemolyzed blood;
blood banks;
animal blood from slaughter houses.

Another object of the invention is to produce globins for food purposes from animal haemoglobins.

The haemoglobin to be treated may be in the native form (for example haemolyzed globular residues), in the non-denatured purified form (for example by anion exchange chromatography of a clarified placental blood), or in the form of a denatured precipitate (for example by selective precipitation with chloroform or sodium caprylate—see LIAUTAUD et coll. Developments in Biological Standardization Vol. 27 1974 pages 107–114; or STEINBUCH et coll. Revue Franc. études chim. et Biol. 1969, XIV, 10, pages 1054–1058).

The invention provides a process for preparing globin from haemoglobin in which there is prepared an alcoholic solution of haemoglobin with an acid pH, characterized in that an alcoholic solution having an acid pH is adsorbed on the active charcoal, preferably at room temperature.

Surprisingly, although the active charcoal is known to highly adsorb the proteins, it fixes the haem and does not adsorb the globin. The yield of globin is close to 100%.

Preferably, the concentration of alcohol, such as for example ethanol or methanol, is at least 40% and preferably 75 to 80%.

In the case where the haemoglobin is available in the form of a precipitate, it is advantageous to take it up in a solution of about 10% (weight/volume). This may be for example effected by addition of water (20% of the total volume) acidification with 3N HCl then addition of 80% of ethanol.

Preferably, the acid pH is lower than 4 and preferably higher than 2, for example around 3. When the pH increases, in particular beyond 4, the active charcoal starts to adsorb appreciable quantities of proteins. Moreover, for excessively acid pHs the amount of proteins recovered drops and a denaturing of the globin is also to be feared.

The choice of the active charcoal is effected by measuring the decolouring power with respect to the haemoglobin. This power is estimated in the ratio R=O.D. 280 nm/O.D. 403 nm. This ratio is 0.26 for the non-depigmented haemoglobin. Powdered active charcoals are particularly preferred and the table appearing in the following description will give examples of commercially available charcoals which give very good results.

Preferably, there is used an optimum quantity of active charcoal which is as small as possible so as to minimize handling. The ratio between the weight of the charcoal and the weight of haemoglobin varies, depending on whether the haemoglobin is in the native state in solution or denatured in the form of a precipitate. It increases in the last-mentioned case and may be for example of the order of 3 g of charcoal for 10 g of haemoglobin precipitate.

The contact time is preferably of the order of 15 hours. This time may vary considerably and is determined in particular by industrial considerations of production and by the size and number of the vessels.

The ionic force is adjusted to a rather low value, for example lower than 0.03M NaCl.

The temperature is preferably no higher than 20° C. in order to avoid alcohol vapours for reasons of safety.

In a particularly advantageous manner, stirring may be effected throughout the contact period, this stirring substantially increasing the yield.

The invention also concerns the purified industrial globins obtained. The decolouring index D.O. 280 nm/D.O. 403 nm may be higher than 10 and the human globin is suitable for therapeutic applications.

Further advantages and features of the invention will be apparent from the following description which is given merely by way of a non-limiting example.

EXAMPLE 1

A denatured haemoglobin precipitate is obtained from placental haemolyzed blood by precipitation with chloroform. The precipitate is taken up by addition of water (20% of the total volume) then acidification with 3N HCl after which the ethanol required for obtaining a concentration of 80% is added. The smallest volume for obtaining the redissolution corresponds to a mixture at 10% (weight/volume); it is this volume which is preferred since it results in the lowest consumption of alcohol. The insoluble fraction is about 33% of the initial precipitate (in the case of a precipitate with sodium caprylate, the mixing rate is 6% and the remaining insoluble fraction is 25% of the initial precipitate).

The pH of the haemoglobin solution is adjusted to 3.3.

The active charcoal chosen is the charcoal of type L 4S prepared by the French company CECA.

The active charcoal is added to the haemoglobin solution at 20° C. in the proportion of 3 g per 10 g of initial haemoglobin precipitate (3.4 g per 10 g in the case of the precipitate obtained with caprylate).

The mixture effected in a vessel is continuously stirred for 15 hours, the apparent pH being 3.3.

The charcoal is then discharged by centrifuging. The alcoholic solution of globin which forms the supernatant is then diluted in an equal volume of water and neutralized by the addition of N soda. After precipitation and the collection of the globin precipitate by centrifuging or filtering, it is observed that the liquid obtained is perfectly clear and uncoloured and lends itself perfectly well to the operations for recycling the alcohol by distillation.

The globin precipitate may then be converted into a perfectly decoloured globin solution by known processes.

EXAMPLE 2

In starting with a purified source of haemoglobin, for example haemoglobin of placental haemolyzed blood from which the immunoglobulins, albumin and possible other plasmatic components have been extracted, or in starting with a haemoglobin solution obtained by lysis of a residue, the haemoglobin is taken up in an ethanol-acid mixture so that, at the end of the addition, the ethanol content is 80% and the apparent pH is 3.1. No precipitate appears and the haemoglobin solution is perfectly clear.

0.2% by weight/volume of active charcoal L4S is added to the solution. The mixture is stirred for 15 hours at a temperature of 20° C. The active charcoal is then eliminated by filtration, for example by means of filtering earth or by centrifuging.

The alcoholic solution of acid globin which appears is completely decoloured. It is then diluted with an equal volume of water and neutralized by the addition of normal soda. After precipitation and collection of the globin precipitate by centrifuging or filtering, it is found that the liquid obtained is perfectly clear and colourless and lends itself perfectly well to the operations for recycling the alcohol by distillation.

The globin obtained is completely depigmented and may be converted into therapeutic derivatives by processes already described.

Comparison of the active charcoals

The following powdered active charcoals were tested:

| Name Properties | Darco KB | Degussa E 114 | Ceca WNCL | Ceca L 3S | Ceca L 4S |
|---|---|---|---|---|---|
| Content of water % | 25 | <10 | 5 | <5 | <5 |
| Content of ashes % CaCO$_3$, K$_2$CO$_3$, Si | 1.3 | <6.5 | <2 | <3.5 | <2 |
| Value of the pH in 20 parts of distilled H$_2$O | 5 | 9–10 | 4.5 | >4.5 | >4.5 |
| Area according to BET m$^2$/g | 1450 | 750 | 1200 | 1200 | 1400 |
| Molasse index | 190 | 100 | — | 80 | 90 |
| Methylene blue index | — | >10 | 20 | 18 | >20 |
| Charcoal particle size | 99% 100 mesh 70% <325 mesh | 80% <40μ | 95% <80μ | 90% <80μ | 90% <80μ |
| Density | 0.110 | 0.365 | 0.580 | 0.200 | 0.180 |

The compared effectiveness of these active charcoals appears in the following table, it being determined by the index R.

| | Name | | | | |
|---|---|---|---|---|---|
| | Darco KG | Degussa E 114 | Ceca WNCL | Ceca L 3S | Ceca L 4S |
| $R = \dfrac{O.D.\ 280\ nm}{O.D.\ 403\ nm}$ | 13 | 8.2 | 6.5 | 12.7 | >15 |

The charcoal L 4S appears to be the most suitable. The quantity of the charcoal is advantageously of the order of 3 g per 10 g of haemoglobin precipitate and preferably less than 6 g.

By way of example, a quantity of 10 metric tons of placentas can supply:
 either about 2.5 metric tons of haemoglobin precipitate denatured by the chloroform or the sodium caprylate,
 or about 250 kg of haemoglobin in aqueous solution.

These values of the preferred process are summarized in the following table:

| Initial quantity of starting material | 2.5 metric tons denatured haemo-globin precipitate | 250 kg of native haemoglobin |
|---|---|---|
| Required volume of ethanol | 30,000 l | 30,000 l |
| Quantity of charcoal L 4S | 800 kg | 60 kg |
| Decolouring of the globin $\dfrac{O.D.\ 280\ nm}{O.D.\ 403\ nm}$ | 10 | 40 |
| Weight of globin obtained | 100 kg | 230 kg |

What is claimed is:

1. A process for preparing globin from haemoglobin comprising preparing an alcoholic solution of haemoglobin at an acid pH, and treating said solution with active charcoal to adsorb the haem in the solution on said active charcoal and thereafter separating the charcoal from the solution.

2. A process according to claim 1, wherein the alcohol concentration is at least 40%.

3. A process according to claim 2, wherein the alcohol concentration is 75 to 80%.

4. A process according to claim 1, wherein ethanol is used.

5. A process according to claim 1, wherein the pH is between 2 and 4.

6. A process according to claim 5, wherein the pH is of the order of 3.

7. A process according to claim 1, wherein the weight of the active charcoal is less than 6 g/10 g of haemoglobin precipitate.

8. A process according to claim 7, wherein the weight of charcoal is of the order of 3 g/10 g of haemoglobin precipitate.

9. A process according to claim 1, wherein the weight of the charcoal is of the order of 0.2% (weight/volume) for a native haemoglobin solution.

10. A process according to claim 1, wherein the active charcoal is powdered charcoal.

11. A process according to claim 10, comprising using an active charcoal CECA of the type L 4S.

12. A process according to claim 1, comprising stirring the mixture during the adsorption.

13. A process according to claim 1, wherein the adsorption lasts 15 hours.

14. A process according to claim 1, carried out at a temperature of the order of 20° C.

15. A process according to claim 1, wherein the ionic force is adjusted to a rather low value.

16. A process according to claim 15, wherein the value of the ionic force is lower than 0.03M NaCl.

17. A process according to claim 1 wherein the separation of the charcoal is by centrifuging.

18. A process according to claim 1 wherein the separation of the charcoal is by filtration.

19. The product produced by the process of claim 1.

* * * * *